United States Patent [19]

Sih

[11] 4,336,392
[45] Jun. 22, 1982

[54] 2-DECARBOXY-2-TETRAZOLYL-PG$_1$ COMPOUNDS

[75] Inventor: John C. Sih, Kalamazoo, Mich.
[73] Assignee: The Upjohn Company, Kalamazoo, Mich.
[21] Appl. No.: 85,618
[22] Filed: Oct. 17, 1979

Related U.S. Application Data

[62] Division of Ser. No. 26,066, Apr. 2, 1979, Pat. No. 4,243,611.
[51] Int. Cl.$^3$ ................ C07D 257/06; C07D 409/08; A61K 31/41
[52] U.S. Cl. ................... 548/253; 424/269
[58] Field of Search .................. 548/253; 542/429

[56] References Cited

U.S. PATENT DOCUMENTS 3,932,389 1/1976 Johnson et al. .............. 548/252
4,064,351 12/1977 Sakai et al. .................. 542/426

*Primary Examiner*—David B. Springer
*Attorney, Agent, or Firm*—Lawrence T. Welch; Robert A. Armitage

[57] ABSTRACT

The present invention provides novel 2-decarboxy-2-tetrazolyl-PG$_1$ compounds, methods for their preparation and pharmacological use for the induction of prostaglandin-like effect.

1 Claim, No Drawings

4,336,392

2-DECARBOXY-2-TETRAZOLYL-PG₁ COMPOUNDS

Cross Reference to Related Applications

The present application is a division of Ser. No. 026,066, filed Apr. 2, 1979, U.S. Pat. No. 4,243,611, issued Jan. 6, 1981.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 2-decarboxy-2-tetrazolyl-PG₁ compounds, a disclosure of the preparation and use of which is incorporated here by reference from U.S. Ser. No. 025,899, filed Apr. 2, 1979, now U.S. Pat. No. 4,228,104, issued Oct. 14, 1980.

PRIOR ART

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

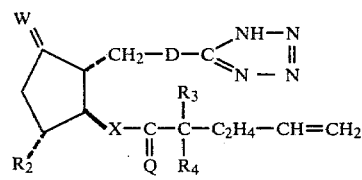

wherein D is
(1) —(CH₂)₃—(CH₂)$_g$—CH₂—,
(2) —(CH₂)₃—CH₂—CF₂—,
(3) —(CH₂)₃—O—CH₂—,
(4) —(CH₂)₂—O—(CH₂)₂—,
(5) —CH₂—O—(CH₂)₃—,

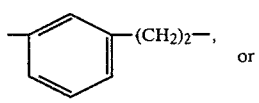

or

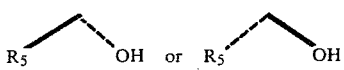

wherein q is zero, one, two, or three; wherein Q is

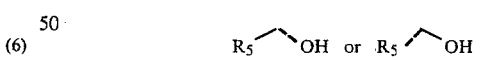

wherein R₅ is hydrogen or methyl, wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro; wherein W is

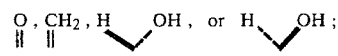

and wherein X is cis- or trans—CH=CH— or —C≡C—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

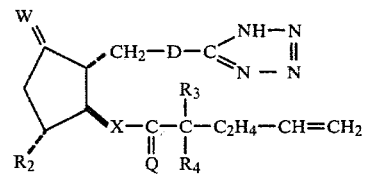

wherein D is
(1) —(CH₂)₃—(CH₂)$_g$—CH₂—,
(2) —(CH₂)₃—CH₂—CF₂—,
(3) —(CH₂)₃—O—CH₂—,
(4) —(CH₂)₂—O—(CH₂)₂—,
(5) —CH₂—O—(CH₂)₃—,

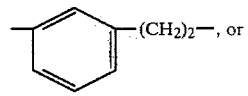

(6)

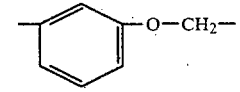

(7)

wherein g is zero, one, two, or three; wherein Q is

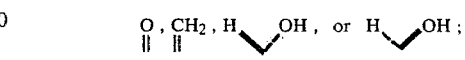

wherein R₅ is hydrogen or methyl, wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro; wherein W is O, CH₂, H⧹/OH, or H⧹/OH;

and wherein X is cis- or trans—CH=CH— or —C≡C—.

* * * * *

UNITED STATES PATENT OFFICE
CERTIFICATE OF CORRECTION

Patent No. 4,336,392　　　　　　　　Dated　22 June 1982

Inventor(s)　John C. Sih

It is certified that error appears in the above-identified patent and that said Letters Patent are hereby corrected as shown below:

Column 1, line 61, "wherein q" should read -- wherein g --.

*Signed and Sealed this*

*Twenty-eighth* Day of *December 1982*

[SEAL]

Attest:

GERALD J. MOSSINGHOFF

*Attesting Officer*　　　*Commissioner of Patents and Trademarks*